United States Patent [19]

Strunk et al.

[11] Patent Number: 4,981,508
[45] Date of Patent: Jan. 1, 1991

[54] 1,4-BENZOXAZIN-3-ONE SUBSTITUTED URACILS

[75] Inventors: Richard J. Strunk; Allyn R. Bell, both of Cheshire, Conn.

[73] Assignee: Uniroyal Chemical Company, Inc., Middlebury, Conn.

[21] Appl. No.: 300,384

[22] Filed: Jan. 23, 1989

[51] Int. Cl.⁵ .................. A01N 43/48; C07D 498/02; C07D 401/00
[52] U.S. Cl. ........................................ 71/92; 544/105; 544/310
[58] Field of Search ..................... 71/92; 544/105, 310

[56] References Cited

U.S. PATENT DOCUMENTS 4,640,707  2/1987  Nagano et al. .................. 71/96
4,812,164  3/1989  Wenger et al. .................. 71/92

FOREIGN PATENT DOCUMENTS 0195346  3/1986  European Pat. Off. ............ 71/92
0255047  7/1987  European Pat. Off. ............ 71/92
0260162  7/1987  European Pat. Off. ............ 71/92

Primary Examiner—Mukund J. Shah
Assistant Examiner—E. C. Ward
Attorney, Agent, or Firm—Glenn E. Karta

[57] ABSTRACT

A compound having the structural formula

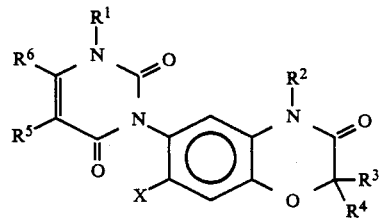

where $R^1$ is hydrogen, $C_1$-$C_4$ alkyl, $C_3$-$C_4$ alkenyl or $C_3$-$C_4$ alkynyl; $R^2$ is $C_1$-$C_4$ alkyl, $C_3$-$C_4$ alkenyl, $C_3$-$C_4$ alkynyl or $(CH_2)_n$—Y; $R^3$ is hydrogen or $C_1$-$C_4$ alkyl, $R^4$ is hydrogen or $C_1$-$C_4$ alkyl; $R^5$ is hydrogen or halogen; $R^6$ is $C_1$-$C_4$ fluoroalkyl; X is hydrogen, fluorine or chlorine; Y is phenyl, cyano or $C_1$-$C_4$ alkoxycarbonyl; and n is 1 or 2 is disclosed. In addition, a process for forming the compound is set forth. A method for controlling weeds which comprises applying a herbicidally effective amount of the compound recited above is also described. Finally, a composition, useful as a herbicide, including the compound of this invention and a suitable carrier therefor is taught.

13 Claims, No Drawings

1,4-BENZOXAZIN-3-ONE SUBSTITUTED URACILS

BACKGROUND OF THE INVENTION

1. Field of the Invention

The subject invention is directed to a new class of 1,4-benzoxazin-3-one substituted uracils. More specifically, the present invention is directed to a class of benzoxazin-3-one substituted uracils having particular utility as pre- and post-emergent herbicides.

2. Background of the Prior Art

Weeds and other undesirable plants undermine the production of useful agricultural crops by inhibiting the production of foliage, fruit or seeds of these useful plants. Weeds cause this undesirable result because of their sharing available light, moisture, nutrients and space with useful crops. Indeed, in many cases weeds exclude light, moisture, nutrients and even space to the useful crops with which they interfere. As a result, the presence of weeds not only reduces the quantity and quality of harvested agricultural crops but, in addition, reduces harvesting efficiency. Thus, it is not surprising that weed control is essential for the successful and economic production of many agronomic and horticultural crops including corn (*Zea mays* L.), cotton (*Gossypium hirsutum* L.) and peanuts (*Archis hypogaea* L.).

In addition to the economic necessity of controlling weeds, to ensure efficient production of useful crops, the control of weeds on noncropped areas is also essential. Weeds present a fire hazard. Many weeds give off pollen which cause serious irritation and illness to a significant percentage of the population afflicted with allergies. Moreover, weeds can cause undesirable drifting of sand, snow and the like. Therefore, suppression of undesirable weed growth is not only advantageous in the case of the successful growth of useful crops but, also, even on lands on which useful crops are not grown. For these reasons, although a large number of compounds possessing herbicidal activity are known, there is a continuing need in the art for the identification and use of new and effective additional compounds to control the growth of unwanted vegetation.

Substituted 3-aryluracils are known in the art. Indeed, substituted 3-aryluracils are disclosed as possessing herbicidal activity. European Patent Application No. 0 195 346 A2 and 0 260 621 A2, both to Wenger et al., disclose two classes of 3-aryluracils useful as herbicidal agents. The compounds of the '346 and '621 applications are uracil compounds substituted at the 3-position with substituted phenyl groups. These compounds are thus structurally far removed from uracil compounds substituted at the 3-position with 1,4-benzoxazin-3-one substituents.

U.S. Pat. No. 4,640,707 to Nagano et al. describes a class of tetrahydrophthalimide compounds, structurally further removed from uracil compounds substituted at the 3-position with substituted 1,4-benzoxazin-3-ones than are the compounds set forth in the above-mentioned European patent applications. This reference is mentioned in that, although significantly removed structurally, the compounds of the '707 patent are recited to be useful as herbicides.

The above remarks establish the continuing need in the art to develop new and improved herbicides to control undesired vegetation that interferes with the successful production of useful plants as well as negating other adverse effects associated with the uncontrolled growth of weeds and the like. These remarks also establish that the class of compounds, the 1,4-benzoxazin-3-one substituted uracils, represent a class of compounds not known in the art. Therefore, the above discussion not only establishes the continuing need to develop new herbicides, it also suggests the desirability of exploiting this new class of organic compounds.

SUMMARY OF THE INVENTION

A new class of compounds, uracils substituted at the 3 position with 1,4-benzoxazin-3-one substituted groups, has now been discovered. These compounds have been found to possess excellent herbicidal properties. These properties are surprisingly effective in either or both pre- and post-emergent applications. That is, the class of compounds of the present invention effectively controls undesired vegetation prior to and after emergence from the soil.

In accordance with the present invention a new class of compounds characterized by the structural formula

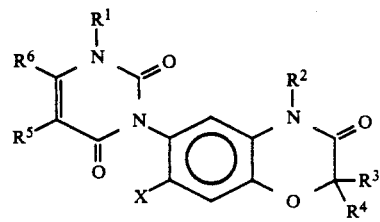

where $R^1$ is hydrogen, $C_1$–$C_4$ alkyl, $C_3$–$C_4$ alkenyl, $C_3$–$C_4$ alkynyl or an alkali metal; $R^2$ is $C_1$–$C_4$ alkyl, $C_3$–$C_4$ alkenyl, $C_3$–$C_4$ alkynyl or $(CH_2)_n$—Y; $R^3$ is hydrogen or $C_1$–$C_4$ alkyl: $R^4$ is hydrogen or $C_1$–$C_4$ alkyl; $R^5$ is hydrogen or halogen: $R^6$ is $C_1$–$C_4$ fluoroalkyl: X is hydrogen, fluorine or chlorine: Y is phenyl, cyano or $C_1$–$C_4$ alkoxycarbonyl; and n is 1 or 2.

In another aspect of the present invention, a process for preparing the above-described class of compounds is described. In the process of forming the above-described class of compounds, with the limitations that $R^1$ is an alkali metal and $R^5$ is limited to hydrogen or fluorine, a compound having the structural formula

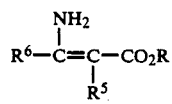

where R is $C_1$–$C_6$ alkyl: and $R^6$ has the meaning given above, is reacted with a strong base. The product of this reaction is reacted with a compound having the structural formula

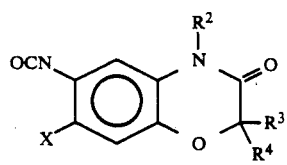

where $R^2$, $R^3$, $R^4$ and X have the meanings given above for the compound of this invention.

In further accordance with the process of making the compound of this invention where $R^1$ is $C_1$–$C_4$ alkyl, $C_3$–$C_4$ alkenyl or $C_3$–$C_4$ alkynyl, that compound is made by reacting an alkylating agent, $R^7-Z^1$, where $R^7$ has the meanings of $R^1$; and $Z^1$ represents a leaving group, is reacted with the product of the compound of the present invention where $R^1$ is an alkali metal.

In still further accordance with the process of making the compound of this invention where $R^1$ is hydrogen, that compound is synthesized by reacting the compound of the present invention where $R^1$ is an alkali metal with a strong acid.

In yet still further accordance with the process of making the compound of this invention where $R^5$ is a halogen other than fluorine, any of the above methods may be employed to produce the compound of this invention where $R^5$ is hydrogen and reacting that compound with the gas of the halogen desired as $R^5$.

The present invention is further directed to a composition comprising the compound having the structural formula

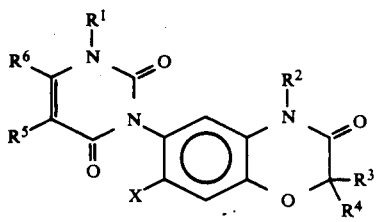

where $R^1$, $R^2$, $R^3$, $R^4$, $R^5$, $R^6$, X, Y and n have the meanings given for the compound of this invention; and a suitable carrier therefor.

In still another aspect of the present invention, a method for controlling weeds and other undesirable vegetation is disclosed. In this method a herbicidally effective amount of a compound having the structural formula given above is applied to the locus to be protected.

DETAILED DESCRIPTION

The present invention, is directed to a class of compounds having the structural formula

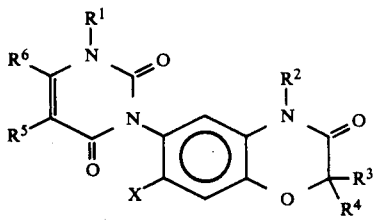

where $R^1$ is hydrogen, $C_1-C_4$ alkyl, $C_3-C_4$ alkenyl, $C_3-C_4$ alkynyl or an alkali metal; $R^2$ is $C_1-C_4$ alkyl, $C_3-C_4$ alkenyl, $C_3-C_4$ alkynyl or $(CH_2)_n-Y$; $R^3$ is hydrogen or $C_1-C_4$ alkyl; $R^4$ is hydrogen or $C_1-C_4$ alkyl; $R^5$ is hydrogen or halogen; $R^6$ is $C_1-C_4$ fluoroalkyl; X is hydrogen, fluorine or chlorine; Y is phenyl, cyano or $C_1-C_4$ alkoxycarbonyl: and n is 1 or 2.

Preferably, the compound of the present invention has the structural formula I where $R^1$ is hydrogen, $C_1-C_4$ alkyl or an alkali metal; $R^2$ is $C_1-C_4$ alkyl, $C_3-C_4$ alkenyl or $C_3-C_4$ alkynyl; $R^3$ is hydrogen or $C_1-C_4$ alkyl: $R^4$ is hydrogen: $R^5$ is hydrogen; $R^6$ is $C_1-C_2$ trifluoroalkyl; Y is phenyl and X is hydrogen or fluorine.

Still more preferably, the compound of the present invention has the structural formula I where $R^1$ is methyl; $R^2$ is $C_1-C_3$ alkyl, 2-propenyl or 2-propynyl; $R^3$ is hydrogen or methyl; Y is phenyl and $R^6$ is trifluoromethyl.

The present invention is also directed to a composition. The composition, having utility as a herbicidal agent, comprises the compound having the structural formula I where $R^1$, $R^2$ $R^3$, $R^4$, $R^5$, $R^6$, X, Y and n have the meanings given for the broadest definition of that compound and a suitable carrier therefor.

Preferably, the composition of the present application comprises a compound having the structural formula I where $R^1$, $R^2$, $R^3$, $R^4$, $R^5$, $R^6$ and X have the meanings given for the preferred embodiment of the compound having the structural formula I and a suitable carrier therefor.

More preferably, the present invention is directed to a composition comprising a compound having the structural formula I where $R^1$, $R^2$, $R^3$ and $R^6$ have the meanings given for the more preferred embodiment and $R^4$, $R^5$ and X have the meanings given for the preferred embodiment of the compound having the structural formula I and a suitable carrier therefor.

The principal utility of the compositions of the present application are as herbicidal compositions. Therefore, in a preferred embodiment, the concentration of the component of the composition defined by the compound having the structural formula I is a herbicidally effective amount of that compound.

As stated above, the composition of the present application includes, as one component thereof, a carrier suitable for admixture with the active agent of the composition, a compound having the structural formula I. The identity of the carrier is very broad. The carrier may be a finely-divided particulate solid, granules, pellets, wettable powders, flowable liquids, soluble powders, aqueous or organic solvents, aqueous or organic dispersants or aqueous or organic emulsifying agents.

Among the materials that can be utilized to produce a solid carrier, that is, a carrier in the form of finely-divided particulates, granules, pellets, wettable powders, soluble powders and the like, are such organic and inorganic materials as appapulgite clay, sand, vermiculite, corn cob, activated carbon and mineral silicates. Among the mineral silicates are mica, talc, pyrophyllite clays and the like.

In the case where the carrier is a solid, a solid composition may be prepared with the active compound impregnated onto the solid carrier. Alternatively, the active compound may be formulated into a wettable powder by grinding it into a fine powder and mixing it with the solid carrier to which a surface active dispersing agent has been added. The wettable powder is then dispersed in water and sprayed onto the soil surface, the crop to be protected and/or the weeds.

The composition may be liquid. A liquid solution is representative of a preferred embodiment of a liquid composition. In the case of a liquid solution, the active compound is dissolved in an aqueous or organic solvent. Among the preferred solvents employed in this invention are aromatic or aliphatic hydrocarbons. Of the hydrocarbons, toluene is particularly preferred.

Of the liquid compositions within the contemplation of this invention, liquid emulsions are more commonly employed than are liquid solutions. An emulsion is preferred because the compound having the structural formula I is an organic compound. Therefore, a composition utilizing the cheapest known carrier, water, is preferred. To provide such a composition the active compound is usually dissolved in an organic solvent to which a surface active dispersing agent is added. Water is added to form the emulsion. The water emulsion is then applied to the locus to be protected, usually by spraying. Alternatively, the emulsion may utilize an organic liquid, such as oil, as the dispersant.

The surface active dispersing agent may be any of those known to those skilled in the art. Examples of appropriate surface active agents are provided in McCutcheron's Detergents and Emulsifiers, Allured Publishing Company, Wedgewood, N.J. (1980).

In still another aspect of the present invention, a method for controlling weeds and undesirable vegetation, which comprises applying a herbicidally effective amount of the compound having the structural formula I, where $R^1$, $R^2$, $R^3$, $R^4$, $R^5$, $R^6$, X, Y and n have the meanings given for the broadest meaning of the compound of this application, to the locus to be protected, is provided.

Preferably, the method of the present invention for controlling weeds comprises applying a herbicidally effective amount of the compound having the structural formula I, where $R^1$, $R^2$, $R^3$, $R^4$, $R^5$, $R^6$ and X have the meanings given for the preferred embodiment of the compound having the structural formula I, to the locus to be protected.

Still more preferably, the method of controlling weeds of the present invention includes the application of a herbicidally effective amount of the compound having the structural formula I, where $R^1$, $R^2$, $R^3$ and $R^6$ have the meanings given for the more preferred embodiment of the compound and $R^4$, $R^5$ and X have the meanings given for the preferred embodiment of the compound, to the locus to be protected.

In a preferred embodiment the herbicidally effective concentration of the active compound of this application, the compound having the structural formula I, ranges between about 1% to about 95% by weight, based on the total weight of the composition. In the preferred embodiment wherein the compound having the structural formula I is utilized as an emulsion herbicidal composition the concentration of the active compound is typically between about 0.002% and about 80% by weight, based on the total weight of the composition.

A herbicidally effective amount of the compound having the structural formula I, in a preferred embodiment of the method of controlling weeds of this invention, typically involves application of from about 0.03 to about 25 pounds of the compound having the structural formula I per acre (about 0.033 to about 28 kilograms per hectare), when the compound is employed as a preemergence herbicide. Application of the preemergence herbicide is typically made to the soil which contains weeds and the desired crop seed. Such application is made either to the surface of the soil or applied 1 to 3 inches (2.5 to 7.5 cm.) under the surface of the soil.

In the event that the method for controlling weeds is undertaken after emergence of the weeds, that is, a method of postemergence herbicidal control is utilized, the amount of the active compound, the compound having the structural formula I, is about 0.03 to about 25 pounds per acres (about 0.033 to about 28 kg/ha). Usually, postemergent application occurs by aerial spraying of the undesired vegetation.

Of course, hard and fast rules regarding concentration of the active compound depends on a multiplicity of factors such as soil type, soil pH, soil organic matter content, the quantity and intensity of rainfall before and after treatment, air and soil temperature, light intensity and light duration per day. All of these factors have an influence of the efficacy of the compound of this invention as a herbicide. Those skilled in the art can, by routine experimentation, readily determine the optimum conditions for employment of the compounds within the contemplation of this invention.

The compound of the present application, the compound having the structural formula I, having the meanings given for the broadest definition of this application, except for the further limitation that $R^1$ is limited to an alkali metal and $R^5$ is limited to hydrogen or fluorine, is prepared by reacting a compound having a structural formula

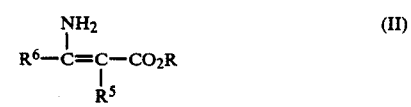

where R is $C_1-C_6$ alkyl: $R^5$ is hydrogen or fluorine: and $R^6$ is $C_1-C_4$ fluoroalkyl, with a strong base at a temperature in the range of between about $-10°$ C. and $25°$ C. The compound having the structural formula II is introduced into this reaction in solution. The solvent in which the compound having the structural formula II is dissolved is an aprotic organic solvent which may be an aliphatic or cyclic ether, an aromatic hydrocarbon, a polar solvent or a mixture of two or all three of these solvent types.

In a preferred embodiment, ethers that may be utilized include 1,2-dimethoxyethane and tetrahydrofuran. In the case where an aromatic hydrocarbon is employed, it is preferably toluene. The preferred aprotic polar solvents are dimethylformamide and dimethylsulfoxide.

The strong base, which is reacted with the compound having the structural formula II, is preferably sodium hydride or an alkali metal alkoxide. In the event that an alkali metal alkoxide is employed, the preferred species is potassium t-butoxide. Of the preferred bases, suitable for reaction with the compound of the structural formula II, sodium hydride is most preferred.

The product of the reaction of the strong base and compound II is, in turn, reacted with an isocyanate compound having the structural formula

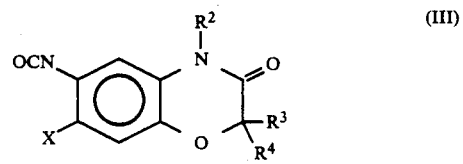

where $R^2$ is $C_1-C_4$ alkyl, $C_3-C_4$ alkenyl, $C_3-C_4$ alkynyl or $(CH_2)_n$—Y; $R^3$ and $R^4$ are independently hydrogen or $C_1-C_4$ alkyl; X is hydrogen, fluorine or chlorine: and Y is phenyl, cyano or $C_1-C_4$ alkoxycarbonyl: and n is 1 or 2. Prior to this reaction, the reaction product of the strong base and the compound having the structural formula II is initially cooled to a temperature between about $-70°$ C. and about $0°$ C. When the desired temperature in this range is reached, the reaction product is reacted with the isocyanate compound.

This reaction between the isocyanate compound and the compound of the reaction product of compound II and a strong base occurs in solution. To accomplish this, any suitable solvent for the isocyanate compound may be utilized. The product of this reaction is the compound having the structural formula I. That compound is separated, by removal of the solvent to dryness, as the alkali metal salt.

It should be appreciated that the isocyanate compounds characterized by structural formula III are prepared by phosgenation of a 1,4-benzoxazine compound having the structural formula

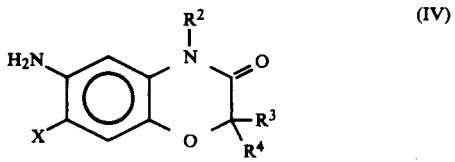

where $R^2$, $R^3$, $R^4$ and X have the meanings given for the compound having the structural formula III. The exact details of the method of preparation are given at page 364 of the text, S. R. Sandler and W. Karol, "Organic Functional Group Preparations," Academic Press, New York (1983). That portion of the text providing this general method is incorporated herein by reference.

It is noted that a compound having the structural formula IV is itself prepared by reducing a substituted 1,4-benzoxazine having the structural formula

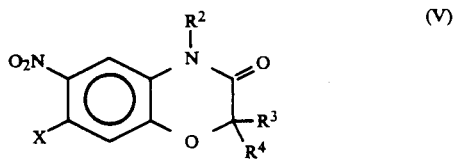

where $R^2$, $R^3$, $R^4$ and X have the meanings given for the intermediate compound of this invention having the structural formula III, with iron as taught in U.S. Pat. No. 4,640,707, incorporated herein by reference.

It is further noted that the description given in the '707 patent describes the reaction of a compound having the structural formula V where $R^2$ is hydrogen. However, compounds having the structural formula V, where $R^2$ is $C_1$–$C_4$ alkyl, $C_3$–$C_4$ alkenyl, $C_3$–$C_4$ alkynyl or $(CH_2)_n$—Y can be prepared by reacting compounds having the structural formula V where $R^2$ is hydrogen with an appropriate alkylating compound in accordance with the procedures set forth in U.S. Pat. No. 4,640,707, already incorporated herein by reference.

The production of compounds having the structural formula V, where $R^2$ and X are hydrogen, can be prepared by the method described in Synthesis 986, International Journal of Methods in Synthetic Organic Chemistry, Georg Thieme Verlag, Stuttgart-New York, 1982, which is incorporated herein by reference.

Other methods for preparing the compound having the structural formula V, where X is fluorine are included in U.S. Pat. No. 4,640,707, incorporated herein by reference, and European Patent Application No. 0 237 899, which is hereby incorporated by reference.

To obtain the compound having the structural formula I where $R^1$ is hydrogen, the compound having the structural formula I where $R^1$ is an alkali metal, is reacted with a strong acid. Although any strong organic or inorganic acid may be employed in this reaction, hydrochloric acid is preferred. The solid product of this acidification reaction is filtered and recrystallized from an appropriate solvent to yield the desired product.

More preferably, the process of forming the compound having the structural formula I, where $R^1$ is hydrogen or an alkali metal and $R^5$ is hydrogen or fluorine, involves the same set of reactions wherein the radicals have the meanings given for the preferred embodiment of the compound having the structural formula I. Still more preferably, the process of forming the compound having the structural formula I involves the same reactions discussed above with the exception that the meaning of the radicals are those given for the more preferred embodiment of the compound having the structural formula I.

In order to make the compound having the structural formula I wherein $R^1$ is not hydrogen but, rather, $C_1$–$C_4$ alkyl, $C_3$–$C_4$ alkenyl or $C_3$–$C_4$ alkynyl, a process is provided where a compound having the structural formula I, where $R^1$ is hydrogen, formed in accordance with the procedure enumerated above, is reacted, in the presence of a solvent selected from the group consisting of alcohols, ketones, ethers or polar aprotic solvents, with a base to form the corresponding salt.

It is emphasized that among the solvents within the contemplation of this invention, ethanol or isopropanol is preferred if the solvent is an alcohol. The preferred aliphatic ketone is acetone. The preferred ethers for use in this reaction are diethyl ether and tetrahydrofuran. Dimethylformamide and dimethylsulfoxide represent the preferred aprotic polar solvents.

The base reacted with the compound having the structural formula I, where $R^1$ is hydrogen, is preferably selected from the group consisting of sodium hydride, an alkali metal alkoxide, an alkali metal carbonate or an organic base. Representative of preferred alkali metal alkoxides and alkali metal carbonates are sodium methoxide, sodium carbonate, and sodium bicarbonate. A preferred organic base is triethylamine. This reaction, which yields a salt of the compound having the structural formula I, occurs at a temperature in the range of between about 0° C. and about 60° C. The time duration of this reaction is a function of the identity of the base and the solvent for the compound having the structural formula I.

The thus formed salt is thereafter alkylated with an alkylating agent having the structural formula

where $R^1$ $C_1$–$C_4$ alkyl, $C_3$–$C_4$ alkenyl or $C_3$–$C_4$ alkynyl; and Z is chlorine, bromine, iodine, methane sulfonate, methyl sulfate or the like. That is, Z represents a leaving group. This alkylation reaction, which occurs at ambient pressure and temperature, occurs over a period ranging from about 0.5 hour to 48 hours. The exact time of reaction depends on the exact identity of the salt of compound I and the hydrocarbyl group defined by $R^1$. Suffice it to say, it is preferred that the reaction be monitored by an analytical method such as nuclear magnetic resonance, infrared spectroscopy or thin-layer chromatography. The product of this alkylation reaction is isolated and obtained by methods known to those skilled in the art.

In an alternate preferred embodiment, a compound having the structural formula I where $R^1$ is $C_1$–$C_4$ alkyl, $C_3$–$C_4$ alkenyl or $C_3$–$C_4$ alkynyl is obtained by reacting the alkali metal salt of the compound I (the compound having the structural formula I where $R^1$ is an alkali metal) with a compound having the structural formula, $R^7$-$Z^1$, where $R^7$ has the same meanings as $R^1$ and $Z^1$ has the same meanings as Z in formula VI. This reaction occurs under the same conditions set forth in the above paragraph for alkylating the compound having the structural formula I.

In yet another preferred embodiment of the process of this invention, wherein a compound of the structural formula I is synthesized, a compound characterized by $R^5$ being a halogen other than fluorine is produced. In that process any compound having the structural formula I, formed in accordance with any of the embodiments taught above, wherein $R^5$ is hydrogen, is reacted with the desired halogen, chlorine, bromine or iodine, in an acidic environment.

The following examples are given to illustrate the spirit of the invention embodied herein. Since these examples are given for illustrative purposes only, they should not be interpreted as limiting the invention to the scope of the examples recited hereinafter.

EXAMPLE 1

Preparation of
3-[2-Methyl-3,4-dihydro-3-oxo-4-(propynyl)-2H-1,4-benzoxazin-6-yl]-6-(trifluoromethyl)-2,4(1H,3H)-pyrimidinedione (Compound No. 1)

A slurry of 1.4 g. of sodium hydride in 25 ml. of dry tetrahydrofuran (THF) was cooled to −10° C. To the cooled and stirred slurry was added a solution of 10.0 g. of ethyl 3-amino-4,4,4-trifluoro-2-butenoate in 50 ml. of THF. The addition of this solution was made over a period of 30 minutes. The resultant light brown reaction mixture was cooled to −70° C. A solution of 13.3 g. of 6-isocyanato-2-methyl-3,4-dihydro-3-oxo-4-(2-propynyl)-2H-1,4-benzoxazine in 75 ml. of THF was added to the chilled reaction mixture over a period of 10 minutes. After stirring at −70° C. for 30 minutes, the temperature was allowed to rise slowly to 10° C. At that point 3.6 ml. of acetic acid was added to the mixture. A beige solid precipitated. 19.0 Grams of the solid was recovered by filtering it from the reaction mixture.

The solid was recrystallized from isopropanol to yield 6.8 g. of 3-[2-methyl-3,4-dehydro-3-oxo-4-(propyl)-2-H-1,4-benzoxazine-6-yl-]6-(trifluoromethyl)-2,4(1H,3H) pyrimidinedione, characterized by a melting point of 277° C. to 278° C.

EXAMPLE 2

Preparation of
1-Methyl-3-[2-methyl-3,4-dihydro-3-oxo-4-(2-propynyl)-2H-1,4-benzoxazin-6-yl]-6-(trifluoromethyl)-2,4(1H,3H)-pyrimidinedione (Compound No. 2)

To a mixture of 30 ml. of dimethylformamide and 0.44 g. of a 60% mineral oil dispersion of sodium hydride (washed with hexane to remove the oil) was added 3.79 g. of the product of Example 1. This addition was conducted at room temperature with stirring over a period of 10 minutes. This addition resulted in the evolution of hydrogen gas. Upon ceasing of gas evolution, 1.5 g. of dimethyl sulfate was added and the reaction mixture was heated at 45° C. for 30 minutes. Analysis of this reaction mixture by thin-layer chromatography (silica, 1/1 ethyl acetate-hexane) established the absence of any starting material. The reaction mixture was poured into 300 ml. of water with stirring. The solid product resulting therefrom was filtered to yield 3.7 g. of a white solid. Preparative liquid chromatography on a Waters [trademark] Prep 500A Liquid Chromatograph using a silica cartridge and 10% ethyl acetate-toluene as eluent afforded 1.5 g. of purified 1-methyl-3-[2-methyl-3,4-dihydro-3-oxo-4-(2-propynyl)-2H-1,4-benzoxazin-6-yl]-6-(trifluoromethyl)-2,4(1H,3H)-pyrimidinedione, characterized by a melting point of 218° C. to 219° C.

EXAMPLE 3

Preparation of
1-Ethyl-3-[2-methyl-3,4-dihydro-3-oxo-4-(2-propynyl)-2H-1,4-benzoxazin-6-yl]-6-trifluoromethyl)-2,4(1H,3H)-pyrimidinedione (Compound No. 3)

A mixture was formed by combining 2.8 grams of the product of Example 1, 3-[2-methyl-3,4-dihydro-3-oxo-4-(2-propynyl)-2H-1,4-benzoxazin-6-yl]-6-(trifluoromethyl)-2,4(1H,3H)-pyrimidinedione, 1.2 g. of sodium bicarbonate, 5.5 g. of iodoethane and 45 ml. of acetone. The mixture was heated at reflux for 44 hours. Analysis at that point by thin-layer chromatography (silica gel, 30% ethyl acetatehexane) established that no starting materials remained unreacted. The reaction mixture product was concentrated by evaporating off the volatile components. The product was then partitioned between water and chloroform. The thus formed organic phase was separated, washed with water and dried over magnesium sulfate. After evaporation of the solvent, 3.2 grams of a beige solid was obtained. Preparative liquid chromatography of this crude product on a silica cartridge using 10% ethyl acetate-toluene yielded 0.6 g. of 1-ethyl-3-[2-methyl-3,4-dihydro-3-oxo-4-(2-propynyl)-2H-1,4-benzoxazin-6-yl]-6-(trifluoromethyl)-2,4(1H,3H)-pyrimidinedione. This product was characterized by a melting point of 205° C. to 207° C.

EXAMPLE 4

Preparation of
3-[4-Ethyl-2-methyl-3,4-dihydro-3-oxo-2H-1,4-benzoxazin-6-yl]-1-sodio-6-(trifluoromethyl)-2,4(1H,3H)-pyrimidinedione (Compound No. 6)

A solution of 15.8 g. of ethyl 3-amino-4,4-4-trifluoro-2-butenoate in 75 ml. of dry THF was added dropwise into a stirred slurry of 3.4 g. of sodium hydride in 50 ml. of THF that had been previously cooled to 0° C. over a period of 30 minutes. The solution resulting from this addition was cooled to −70° C. in a dry-ice/acetone bath. A solution of 20.0 g. of 4-ethyl-6-isocyanato-2-methyl-3,4-dihydro-3-oxo-2H-1,4-benzoxazine in 50 ml. of THF was added to the chilled solution over a period of 25 minutes. The reaction mixture was allowed to warm slowly to room temperature. At room temperature, the reaction mixture was stirred for 18 hours. The solid product in the reaction mixture was filtered, treated with diethyl ether and refiltered to yield 10.6 g. of a fine white solid having a melting point in excess of 230° C.

The NMR data (included in Table 1) was consistent with the assigned structure of this compound in that an exact melting point was not obtained. It is noted that the NMR spectrum indicated the presence of small amount of THF, diethyl ether and water but was otherwise sufficiently pure for conversion to the N-alkyl compound.

EXAMPLE 5

Preparation of
3-[4-ethyl-2-methyl-3,4-dihydro-3-oxo-2H-1,4-benzoxazin-6-yl]-1-methyl-6-(trifluoromethyl)-2.4(1H,3H)-pyrimidinedione (Compound No. 7)

Eight grams of the product of Example 4, 3-[4-ethyl-2-methyl-3,4-dihydro-3-oxo-2H-1,4-benzoxazin-6-yl]-1-sodio-6-(trifluoromethyl)-2,4(1H,3H)-pyrimidinedione, and 5.2 g. of iodomethane in 100 ml. of dry acetone were stirred together at 25° C. for four days. The white solid that formed as the product of this reaction was filtered and washed with cold acetone to yield 3.8 g. of 3-[4-ethyl-2-methyl-3,4-dihydro-3-oxo-2H-1,4-benzoxazin-6-yl]-1-methyl-6-(trifluoromethyl)-2,4(1H,3H)-pyrimidinedione. Recrystallization of the filtrate residue from ethanol yielded an additional 1.9 g. of the product. The pyrimidinedione product of this example was characterized by a melting point of 221° C. to 222° C.

EXAMPLE 6

Preparation of
1-Methyl-3-[2-methyl-3,4-dihydro-3-oxo-4-(1-propyl)-2H-1,4-benzoxazin-6-yl]-6-(trifluoromethyl)-2,4(1H,3H)-pyrimidinedione (Compound No. 10)

Four grams of 1-methyl-3-[2-methyl-3,4-dihydro-3-oxo-4-(2-propenyl)-2H-1,4-benzoxazin-6-yl]-6-(trifluoromethy-1)-2,4(1H,3H)-pyrimidinedione was prepared by the methods outlined in Examples 4 and 5 using the appropriate starting materials. The four grams so formed was placed in a 500 ml. glass hydrogenation vessel along with 200 ml. of ethyl acetate and 400 mg. of a 5% palladium-carbon catalyst. Hydrogenation was carried out in a Parr [trademark] hydrogenation aapparatus by reacting the contents of the glass hydrogenation vessel with hydrogen (45 psi) with shaking. Hydrogenation was completed within 15 minutes. The catalyst was filtered off and the solvent evaporated to yield 3.9 g. of 1-methyl-3-[2-methyl-3,4-dihydro-3-oxo-4-(1-propyl)-2H-1,4-benzoxazin-6-yl]-6-(trifluoromethyl)-2,4(1H,3H)-pyrimidinedione which was characterized by a melting point of 202° C. to 204° C.

EXAMPLE 7

Preparation of Compound Nos. 4, 5, 8, 9 and 11

Additional compounds within the scope of this invention, Compounds Nos. 4, 5, 8, 9 and 11, were prepared using the procedures set forth in Examples 1-6. These compounds are suxmarized in Table I below. The table includes structural identification and melting point and NMR characterizing data. For completeness, the compounds formed in Examples 1-6, Compounds 1, 2, 3, 6, 7 and 10, respectively, are also included in the table.

TABLE 1

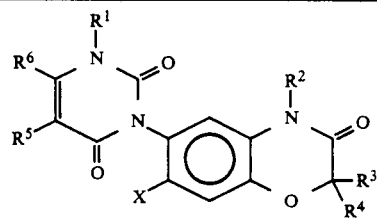

| Cpd. No. | $R^1$ | $R^2$ | $R^3$ | $R^4$ | $R^5$ | $R^6$ | X | MP, °C. | NMR (Solvent)δ(ppm) |
|---|---|---|---|---|---|---|---|---|---|
| 1 | H | $CH_2C\equiv CH$ | $CH_3$ | H | H | $CF_3$ | H | 277-278 | (acetone $d_6$)1.54(d,3H), 2.68(t,1H),4.71(m,3H), 6.23(s,1H),7.00(m,1H), 7.10(m,1H),7.23(d,1H). |
| 2 | $CH_3$ | $CH_2C\equiv CH$ | $CH_3$ | H | H | $CF_3$ | H | 218-219 | ($CDCl_3$)1.60(d,3H),2.26 (t,1H),3.54(s,3H),4.62 (m,3H),6.37(s,1H),6.88 (dd,1H),7.02(d,1H),7.12 (d,1H). |
| 3 | $C_2H_5$ | $CH_2C\equiv CH$ | $CH_3$ | H | H | $CF_3$ | H | 205-207 | ($CDCl_3$)1.37(t,3H),1.61 (d,3H),2.26(t,1H),4.02 (q,2H),4.65(m,3H),6.35 (s,1H),6.85(dd,1H), 7.02(d,1H),7.12(d,1H). |
| 4 | Na | $CH_3$ | $CH_3$ | H | H | $CF_3$ | H | dec 280 | (acetone $d_6$+$DMSOd_6$) 1.51(d,3H),3.30(s,3H), 4.66(q,1H),5.69(s,1H), 6.77(dd,1H), 6.91 (d,1H),6.97(d,1H). |
| 5 | $CH_3$ | $CH_3$ | $CH_3$ | H | H | $CF_3$ | H | 268-270 | ($CDCl_3$)1.60(d,3H),3.32 (s,3H),3.55(d,3H),4.68 (q,1H),6.38(s,1H),6.79 (d,1H),6.84(dd,1H), 7.10(d,1H). |
| 6 | Na | $C_2H_5$ | $CH_3$ | H | H | $CF_3$ | H | dec 235 | (acetone $d_6$)1.16 (t,3H),1.49(d,3H), 3.92(q,2H),4.62(q,1H), 5.73(s,1H),6.75 (dd,1H),6.94(m,2H). |
| 7 | $CH_3$ | $C_2H_5$ | $CH_3$ | H | H | $CF_3$ | H | 221-222 | ($CDCl_3$)1.24(t,3H),1.58 (d,3H),3.55(d,3H),3.92 (m,2H),4.66(q,1H),6.38 (s,1H),6.85(m,2H),7.20 |

TABLE 1-continued

| Cpd. No. | R¹ | R² | R³ | R⁴ | R⁵ | R⁶ | X | MP, °C. | NMR (Solvent)δ(ppm) |
|---|---|---|---|---|---|---|---|---|---|
| 8 | Na | CH₂CH=CH₂ | CH₃ | H | H | CF₃ | H | | (d,1H). (acetone d₆)1.51 (d,3H),4.46(m,2H), 4.69(q,1H),5.12(m,2H), 5.74(s,1H),5.84(m,1H), 6.77(dd,1H),6.86 (d,1H),6.95(d,1H). |
| 9 | CH₃ | CH₂CH=CH₂ | CH₃ | H | H | CF₃ | H | 197–198 | (CDCl₃)1.61(d,3H),3.55 (s,3H),4.50(m,2H),4.70 (q,1H),5.21(m,2H),5.85 (m,1H),6.36(s,1H),6.78 (d,1H),6.84(dd,1H), 7.10(d,1H). |
| 10 | CH₃ | CH₂CH₂CH₃ | CH₃ | H | H | CF₃ | H | 202–204 | (CDCl₃)0.95(t,3H),1.58 (d,3H),1.65(m,2H),3.56 (s,3H),3.84(t,2H),4.66 (q,1H),6.38(s,1H),6.77 (d,1H),6.84(dd,1H),7.09 (d,1H). |
| 11 | Na | CH₂C≡CH | CH₃ | H | H | CF₃ | H | dec 230 | (acetone d₆)1.52(d,3H), 2.67(t,1H),4.65(m,3H), 5.75(s,1H),6.80(dd,1H), 6.99(d,1H),7.04(d,1H). |
| 12 | CH₃ | CH₂C₆H₅ | H | H | H | CF₃ | F | | (CDCl₃)3.50(d,3H), 4.76(s,2H),5.10(s,2H), 6.29(s,1H),6.72(d,1H), 6.90(d,1H),7.25(m,5H). |

EXAMPLE 8

Preemergence Control

Compounds made in accordance with the present invention, as tabulated in Table I, were tested to determine their effectiveness as preemergence herbicides. In this test 300 mg. of each of the compounds tested were dissolved in acetone (10 ml.). The solution was stabilized by adding 30 mg. of the emulsifying agent, ethoxylated sorbitan monolaurate, and 90 ml. of distilled water to each of the thus formed solutions of the compounds of this invention. Ten milliliters of each of the thus formed 3,000 ppm stock solutions were diluted to a concentration of 250 ppm by the addition of distilled water.

The compounds were tested by drenching 46 ml. of each of the 250 ppm emulsions, at a rate of 10 pounds per acre (11.2 kg/ha), onto the surface of soil disposed in 4½ inch (11.25 cm) plastic pots wherein seeds of the following weeds had been planted: velvet leaf (*Abutilon theophrasti* Medic.) (VL), jimsonweed (*Datura stramonium* L.) (JW), tall morningglory (*Ipomea purpurea* L. Roth) (TM), switchgrass (*Panicum virgatum* L.) (SG), barnyard grass (*Echinolchloa crus-galli* (L.) Beauv.) (BG), green foxtail (*Setaria viridis*) (L.) Beauv.) (GF).

Percent control of each of these weeds was determined two weeks after treatment by comparison with untreated controls. The results of these tests are summarized in Table II. The data in Table II indicates good to excellent herbicidal efficacy exhibited by the compounds of this invention.

TABLE II

Preemergence Activity (% Control at 11.2 kg/ha)

| Cpd. No. | VL | JW | TM | BG | SG | GF |
|---|---|---|---|---|---|---|
| 1 | 0 | 0 | 80 | 0 | 25 | 0 |
| 2 | 100 | 100 | 100 | 100 | 100 | 100 |
| 3 | 100 | 100 | 100 | 100 | 100 | 100 |
| 4 | 100 | 0 | 50 | 0 | 0 | 50 |
| 5 | 100 | 0 | 100 | 100 | 100 | 100 |
| 6 | 0 | 0 | 0 | 0 | 0 | 0 |
| 7 | 100 | 100 | 100 | 100 | 100 | 100 |
| 8 | NT | NT | NT | NT | NT | NT |
| 9 | 100 | 100 | 100 | 100 | 100 | 100 |
| 10 | 100 | 100 | 100 | 100 | 100 | 100 |
| 11 | 100 | 0 | 95 | 30 | 50 | 100 |
| 12 | 100 | 100 | 100 | 100 | 100 | 100 |

NT = Not Tested

EXAMPLE 9

Postemergence Control

To illustrate the effectiveness of the compounds of this invention as postemergence herbicides, a 3,000 ppm solution, prepared in accordance with the procedure enumerated in Example 8, was applied to foliage of each of the weeds enumerated in Example 8. This was accomplished by wetting the foliage of each of these weeds to the drip point with the above-described solutions applied to the foliage as an atomized spray employing a DeVilbiss [trademark] sprayer. The spraying of the weed foliage occurred six days after foliage emergence. Two weeks after the treatment with the compounds of this invention, percent weed control was determined. Again, percent weed control was determined by comparison with untreated controls. The results of this testing are summarized in Table III.

TABLE III

| | Postemergence Activity (% Control at 3000 ppm) | | | | | |
|---|---|---|---|---|---|---|
| Cpd. No. | VL | JW | Tm | BG | SG | GF |
| 1 | 70 | 100 | 100 | 75 | 60 | 55 |
| 2 | 100 | 100 | 100 | 100 | 100 | 100 |
| 3 | 100 | 100 | 100 | 100 | 100 | 100 |
| 4 | 0 | 0 | 35 | 15 | 0 | 0 |
| 5 | 100 | 65 | 100 | 75 | 35 | 55 |
| 6 | 0 | 0 | 10 | 10 | 5 | 5 |
| 7 | 100 | 100 | 100 | 100 | 100 | 100 |
| 8 | NT | NT | NT | NT | NT | NT |
| 9 | 100 | 100 | 100 | 100 | 100 | 100 |
| 10 | 100 | 100 | 100 | 100 | 100 | 90 |
| 11 | 5 | 35 | 95 | 70 | 20 | 25 |
| 12 | 100 | NT | 100 | 100 | 100 | 100 |

NT = Not Tested

The above preferred embodiments and examples are given to illustrate the scope and spirit of the present invention. These preferred embodiments and examples will make apparent, to those skilled in the art, other embodiment and examples. These other embodiments and examples are within the contemplation of the subject invention. Therefore, the scope of the present invention should be limited only by the appended claims.

What is claimed is:

1. A compound having the structural formula

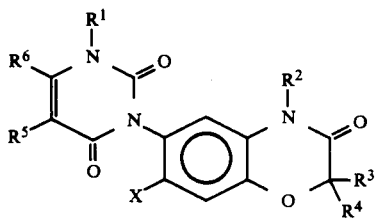

wherein $R^1$ is hydrogen, $C_1$-$C_4$ alkyl, $C_3$-$C_4$ alkenyl, $C_3$-$C_4$ alkynyl or an alkali metal: $R^2$ is $C_1$-$C_4$ alkyl, $C_3$-$C_4$ alkenyl, $C_3$-$C_4$ alkynyl or $(CH_2)_n$—Y: $R^3$ is hydrogen or $C_1$-$C_4$ alkyl: $R^4$ is hydrogen or $C_1$-$C_4$ alkyl; $R^5$ is hydrogen or halogen: $R^6$ is $C_1$-$C_4$ fluoroalkyl; X is hydrogen, fluorine or chlorine: Y is phenyl, cyano or $C_1$-$C_4$ alkoxycarbonyl: and n is 1 or 2.

2. A compound in accordance with claim 1 wherein $R^1$ is hydrogen, $C_1$-$C_4$ alkyl or an alkali metal; $R^2$ is $C_1$-$C_4$ alkyl, $C_3$-$C_4$ alkenyl or $C_3$-$C_4$ alkynyl; $R^3$ is $C_1$-$C_4$ alkyl; $R^4$ is hydrogen; $R^5$ is hydrogen; $R^6$ is $C_1$-$C_2$ trifluoroalkyl; and X is hydrogen.

3. A compound in accordance with claim 2 wherein $R^1$ is hydrogen, $C_1$-$C_2$ alkyl or sodium; $R^2$ is $C_1$-$C_2$ alkyl, 2-propenyl or 2-propynyl: $R^3$ is $C_1$-$C_2$ alkyl; and $R^6$ is trifluoromethyl.

4. A compound in accordance with claim 1 wherein $R^1$ is an alkali metal; and $R^5$ is hydrogen or fluorine.

5. A compound in accordance with claim 1 wherein $R^5$ is chlorine, bromine or iodine.

6. A compound in accordance with claim 1 wherein $R^1$ is hydrogen; and $R^5$ is hydrogen or fluorine.

7. A compound in accordance with claim 1 wherein $R^1$ is $C_1$-$C_4$ alkyl, $C_3$-$C_4$ alkenyl or $C_3$-$C_4$ alkenyl; $R^5$ is hydrogen or fluorine; and $R_2$ is $(CH_2)_n$—Y, Y is phenyl, n is 1.

8. A composition comprising the compound of claim 1 and a suitable carrier therefor.

9. A composition comprising the compound of claim 2 and a suitable carrier therefor.

10. A composition comprising the compound of claim 3 and a suitable carrier therefor.

11. A method for controlling weeds comprising applying a herbicidally effective amount of the compound of claim 1 to the locus to be protected.

12. A method for controlling weeds comprising applying a herbicidally effective amount of the compound of claim 2 to the locus to be protected.

13. A method for controlling weeds comprising applying a herbicidally effective amount of the compound of claim 3 to the locus to be protected.

* * * * *